United States Patent [19]

Chu et al.

[11] Patent Number: 4,665,250
[45] Date of Patent: May 12, 1987

[54] PROCESS FOR CONVERTING LIGHT OLEFINS TO GASOLINE, DISTILLATE AND LUBE RANGE HYDROCARBONS

[75] Inventors: Cynthia T. W. Chu, Pennington, N.J.; Ernest W. Valyocsik, Yardley, Pa.

[73] Assignee: Mobil Oil Corporation, New York, N.Y.

[21] Appl. No.: 832,615

[22] Filed: Feb. 24, 1986

[51] Int. Cl.$^4$ .................................. C07C 2/12
[52] U.S. Cl. ................... 585/415; 585/407; 585/533
[58] Field of Search .......... 585/415, 407, 533

[56] References Cited

U.S. PATENT DOCUMENTS

| | | | |
|---|---|---|---|
| 4,021,502 | 5/1977 | Plank et al. | 585/533 |
| 4,126,644 | 11/1978 | Caesar et al. | 208/135 |
| 4,150,062 | 4/1979 | Garwood et al. | 585/415 |
| 4,211,640 | 7/1980 | Garwood et al. | 208/255 |
| 4,227,992 | 10/1980 | Garwood et al. | 208/46 |
| 4,375,573 | 3/1983 | Young | 585/467 |
| 4,397,827 | 8/1983 | Chu | 423/326 |
| 4,423,021 | 12/1983 | Rollmann et al. | 423/333 |
| 4,450,311 | 5/1984 | Wright et al. | 585/415 |
| 4,456,779 | 6/1984 | Owen et al. | 585/415 |
| 4,511,747 | 4/1985 | Wright et al. | 585/415 |
| 4,524,232 | 6/1985 | Chester et al. | 585/517 |
| 4,542,251 | 9/1985 | Miller | 585/533 |
| 4,547,612 | 10/1985 | Tabak | 585/533 |
| 4,547,613 | 10/1985 | Garwood et al. | 585/415 |
| 4,554,396 | 11/1985 | Chang et al. | 585/531 |
| 4,585,747 | 4/1986 | Valyocsik | 502/62 |

*Primary Examiner*—Asok Pal
*Attorney, Agent, or Firm*—Alexander J. McKillop; Michael G. Gilman; Lowell G. Wise

[57] ABSTRACT

A process is provided for converting light olefin to gasoline, distillate and lube range hydrocarbons which comprises contacting a lower olefin feedstock with acidic zeolite ZSM-48 at elevated pressure and temperature to provide product containing gasoline and distillate range hydrocarbons and a 650° F.+ lube fraction.

19 Claims, No Drawings

PROCESS FOR CONVERTING LIGHT OLEFINS TO GASOLINE, DISTILLATE AND LUBE RANGE HYDROCARBONS

BACKGROUND OF THE INVENTION

This invention relates to the manufacture of gasoline, distillate and lubricant range hydrocarbons from olefins. In particular, a feedstock containing one or more lower olefins is converted in the presence of acidic crystalline zeolite ZSM-48 to heavier aliphatic hydrocarbons.

Conversion of olefins to gasoline and/or distillate products is disclosed in U.S. Pat. Nos. 3,960,978 and 4,021,502 wherein gaseous olefins in the range of ethylene to pentene, either alone or in admixture with paraffins, are converted into an olefinic gasoline blending stock by contacting the olefins with a catalyst bed made up of a ZSM-5 type zeolite. U.S. Pat. No. 4,126,644 discloses the conversion of $C_{5-10}$ olefins over ZSM-5 to produce higher boiling products including a 650° F+ lube fraction. In U.S. Pat. No. 4,227,992 the operating conditions for the Mobil Olefin to Gasoline/Distillate (MOGD) process for selective conversion of $C_3+$ olefins to mainly aliphatic hydrocarbons is disclosed. In a related manner, U.S. Pat. Nos. 4,150,062 and 4,211,640 disclose a process for converting olefins to gasoline components. From U.S. Pat. Nos. 4,397,827 and 4,423,021 it is known that ZSM-48 is useful, inter alia, for the conversion of alcohols, e.g., methanol, to hydrocarbon.

SUMMARY OF THE INVENTION

In accordance with the present invention, a process is provided for converting light olefin to gasoline, distillate and lube range hydrocarbons which comprises contacting a lower olefin feedstock, e.g., one containing predominantly $C_{2-8}$ olefin(s) with acidic zeolite ZSM-48 at elevated pressure and temperature to provide a product containing gasoline and distillate range hydrocarbons and a 650° F+ lube fraction.

DESCRIPTION OF THE PREFERRED EMBODIMENTS

The catalyst composition useful in the process of this invention comprises acidic zeolite ZSM-48. This catalyst and a method for its preparation are described in each of U.S. Pat. No. 4,375,573, 4,397,827 and 4,423,021. The crystal composition of the as-synthesized zeolite ZSM-48 can be identified, in terms of moles of anhydrous oxides per 100 moles of silica as follows:

(0.05 to 5)$R_2O$:(0.1 to 10)$M_{2/n}O$:(0.2 to 1)$Me_2O_3$:(100)$SiO_2$ wherein R is a cation derived from an organic directing agent as more fully described, M is a cation having the valence n and $Me_2O_3$ is an oxide of a trivalent metal, e.g., aluminum, iron, gallium boron, or combination thereof, and wherein the composition is characterized by the distinctive X-ray diffraction pattern as shown in Table I below.

In accordance with the synthesis method of U.S. Pat. No. 4,397,827, the organic directing agent is selected to be a mixture of a $C_{2-12}$, and preferably a $C_{3-5}$, alkylamine and a tetramethyl ammonium compound. The original cations can be replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, metals of Groups II and VIII of the Periodic Table and manganese.

The X-ray diffraction pattern of the silico-crystal of the present invention has the significant lines shown in Table 1 and is further characterized by the fact that it exhibits a singlet line within the range of 11.8±0.2 Angstrom units. The novel crystal of this invention does not have more than one X-ray diffraction line at 11.8±0.2 Angstrom units. The presence of only a singlet line at the indicated spacing structurally distinguishes the instant material from closely related materials such as ZSM-12 (U.S. Pat. No. 3,832,449) which has a doublet (two lines) at 11.8±0.2 Angstrom units and high silica ZSM-12 (U.S. Pat. No. 4,104,294) which also exhibits a doublet at 11.8±0.2 Angstrom units.

TABLE 1

| Characteristic Lines of ZSM-48* | |
|---|---|
| d(A) | Relative Intensity ($I/I_o$) |
| 11.8 ± 0.2 | S |
| 10.2 ± 0.2 | W-M |
| 7.2 ± 0.15 | W |
| 4.2 ± 0.08 | VS |
| 3.9 ± 0.08 | VS |
| 3.6 ± 0.06 | W |
| 3.1 ± 0.05 | W |
| 2.85 ± 0.05 | W |

*In the calcined, sodium-exchanged form.

These values were determined by standard techniques. The radiation was the K-alpha doublet of copper, and a diffractometer equipped with a scintillation counter and a strip chart pen recorder was used. The peak heights, I, and the positions as a function of two times theta, where theta is the Bragg angle, were read from the spectrometer chart. From these, the relative intensities, 100 $I/I_o$, where $I_o$ is the intensity of the strongest line or peak, and d (obs.), the interplanar spacing in A corresponding to the recorded lines, were calculated. In Table 1 the relative intensities are given in terms of the symbols W=weak, VS=very strong, M=medium and W-S=weak-to-strong (depending on the cationic form). Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Employing the procedure described in U.S. Pat. No. 4,397,827, Zeolite ZSM-48 can be obtained from a crystallization reaction medium containing a source of silica, a mixture of a $C_{2-12}$ alkylamine, and a tetramethyl ammonium compound as the directing agent $R_2O$, a source of $M_{2/n}O$, e.g., an alkali metal oxide or source thereof such as sodium silicate, silica hydrosol, silica gel or sodium hydroxide and optionally, a source of metal oxide(s) $Me_2O_3$ or source thereof such as alumina gel, aluminum sulfate, iron sulfate, gallium oxide, etc. and water, and preferably having a composition, in terms of mole ratios of oxides, falling within the following ranges:

| REACTANTS | BROAD | PREFERRED |
|---|---|---|
| $Me_2O_3/SiO_2$ | greater than 0.002 | 0.002 to 0.01 |
| $M_{2/n}O/SiO_2$ | 0.01 to 1.0 | 0.1 to 0.5 |
| $R_2O/SiO_2$ | 0.005 to 0.5 | 0.005 to 0.25 |
| $OH^-/SiO_2$ | 0.01 to 0.5 | 0.05 to 0.2 |
| $H_2O/SiO_2$ | 10 to 200 | 20 to 100 | and maintaining the mixture at 80°-200° C. until crystals of the zeolite are formed. The molar ratio of $C_2$-$C_{12}$ alkylamine to tetramethyl ammonium compound is not narrowly critical and can range from 1:1 to 10:1. The tetramethyl ammonium compound can include the hydroxide or halide with the chloride being particularly preferred. Perferably, crystallization is carried out under pressure in an autoclave or static bomb reactor, at 80° to 200° C. with, or without, seeding. Thereafter, the crystals are separated from the liquid and recovered.

The catalytic activity of ZSM-48 synthesized in the foregoing manner is relatively low for some types of conversions including the conversion of olefin to gasoline, distillate and lube range hydrocarbons. It has been found that when the crystalline zeolite ZSM-48 is prepared with a linear diquaternary ammonium compound as the organic directing agent, this zeolite, while retaining the X-ray diffraction pattern characteristic of ZSM-48, exhibits silica/alumina mole ratios over a wide range and significantly enhanced catalytic activity for the conversion process herein. In addition, the reaction mixture for preparing ZSM-48 in accordance with the method of U.S. Pat. No. 4,397,827, i.e., employing an organic nitrogen-containing directing agent described as a mixture of $C_2$-$C_{12}$ alkylamine and the tetramethylammonium compound, requires a silica/alumina mole ratio of at least about 500 to avoid product contamination with other silicates, notably crystalline silicate ZSM-5 or ZSM-11. The improved zeolite synthesis method more fully described hereinafter allows the reaction mixture silica/alumina mole ratio to be much less than 500, e.g., as low as about 100, to produce relatively pure ZSM-48, and as such, is a preferred method for preparing the ZSM-48 catalyst employed in the process of this invention. It is noted, however, that the reaction mixture silica/alumina mole ratio in this improved method is critical, since at less than about 100, a different crystalline silicate tends to form in place of the ZSM-48.

The organic directing agent required of the improved method is a linear diquaternary ammonium compound expressed by the formula:

$$[(R')_3N^+(Z)_mN^+(R')_3](X^-)_2$$

wherein R' is alkyl of from 1 to 20 carbon atoms, heteroalkyl of from 1 to 20 carbon atoms, aryl, heteroaryl, cycloalkyl of from 3 to 6 carbon atoms, cycloheteroalkyl of from 3 to 6 carbon atoms, or combinations thereof; N is the quadricoordinate element nitrogen, or the heteroatom nitrogen in an alicyclic, heteroalicyclic or heteroaromatic structure; X is an anion (e.g. fluoride, chloride, bromide, iodide, hydroxide, acetate, sulfate, carboxylate, etc.); Z is a bridging member selected from the group consisting of alkyl of from 1 to 20 carbon atoms, alkenyl of from 2 to 20 carbon atoms, aryl, heteroalkyl of from 1 to 20 carbon atoms, heteroalkenyl of from 2 to 20 carbon atoms and heteroaryl; and m is 5, 6, 8, 9 or 10. When N is a heteroatom in an alicyclic, heteroalicyclic or heteroaromatic structure, such structure may be, as non-limiting examples,

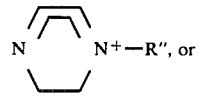

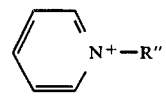

I wherein R" is alkyl of from 1 to 20 carbon atoms, heteroalkyl of from 1 to 20 carbon atoms, aryl, heteroaryl, cycloalkyl of from 3 to 6 carbon atoms or cycloheteroalkyl of from 3 to 6 carbon atoms.

Non-limiting examples of such linear diquaternary compounds include:

$[(CH_3)_3N^+(CH_2)_6N^+(CH_3)_3](Cl^-)_2$,
$[(C_3H_7)_3N^+(CH_2)_6N^+(CH_3H_7)_3](Cl^-)_2$,
$[(C_6H_5)_3N^+(C_2H_4)_6N^+(C_6H_5)_3](OH^-)_2$,
$[(C_{18}H_{37})_3N^+(C_2H_2)_6N^+(CH_3)_3](Br^-)_2$,
$[(C_6H_5)_3N^+(CH_2)_6N^+(CH_3)_3](OH^-)_2$,
$[(C_6H_5)_3N^+(C_2H_2)_6N^+(CH_3)_3](Cl^-)_2$.

Particularly preferred diquaternary compounds have X being halide, e.g., chloride, bromide or iodide, and R' and Z being lower alkyl of 1 to 4 carbon atoms, e.g., methyl, ethyl, propyl or butyl.

Utilizing the foregoing preferred method, ZSM-48 is preferably obtained from the following crystallization reaction medium having a composition, in terms of mole ratios, falling within the following ranges:

| | Broad | Preferred |
|---|---|---|
| $SiO_2/Me_2O_3$ | at least 100 | 100 to 500 |
| $H_2O/SiO_2$ | 10 to 200 | 20 to 100 |
| $OH^-/SiO_2$ | 0 to 1.0 | 0.1 to 0.5 |
| $M^+/SiO_2$ | 0. to 2.0 | 0.1 to 1.0 |
| $R/SiO_2$ | .005 to 2.0 | 0.1 to 1.0 |

Aside from the respects already noted, the improved crystallization method employing a linear diquaternary ammonium compound as the organic directing agent can follow the synthesis procedures described in U.S. Pat. No. 4,397,827.

Prior to its use, synthetic ZSM-48 should be dehydrated at least partially. This can be done by heating to a temperature in the range of from about 200° C. to about 600° C. in an inert atmosphere, such as air, nitrogen, etc. and at atmospheric or subatmospheric pressures for between 1 to 48 hours. Dehydration can also be performed at lower temperature merely by placing the catalyst in a vacuum, but a longer time is required to obtain sufficient amount of dehydration. ZSM-48 is formed in a wide variety of particle sizes. Generally speaking, the particles can be in the form of a powder, a granule, or a molded product, such as extrudate having a particle size sufficient to pass through a 2 mesh (Tyler) screen and be retained on a 400 mesh (Tyler) screen. In cases where the catalyst is molded, such as by extrusion, the crystalline silicate can be extruded before drying or dried or partially dried and then extruded.

As in the case of many other zeolite catalysts, it may be desired to incorporate the ZSM-48 with another material resistant to the temperatures and other conditions employed in the conversion process herein. Such matrix materials include active and inactive materials and synthetic or naturally occurring zeolites as well as inorganic materials such as clays, silica and/or metal oxides, e.g. alumina. The latter may be either naturally occuring or in the form of gelatinous precipitates, sols or gels including mixtures of silica and metal oxides. Use of a material in conjunction with the ZSM-48, i.e. combined therewith, which is active, may enhance the conversion and/or selectivity of the catalyst herein. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g., bentonite and kaolin. These materials, i.e., clays, oxides, etc., function, in part, as binders for the catalyst. It is desirable to provide a catalyst having good crush strength, because in a petroleum refinery the catalyst is often subject to rough handling which tends to break the catalyst down into powder-like materials which cause problems in processing.

Naturally occurring clays which can be composited with ZSM-48 include the montmorillonite and kaloin families which include the sub-bentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoiong materials, ZSM-48 can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline silicate ZSM-48 and inorganic oxide gel matrix vary widely with the crystalline silicate content ranging from about 1 to about 90 percent by weight, and more usually in the range of about 2 to about 50 percent by weight of the composite.

EXAMPLES 1–15

Except as noted below, these examples illustrate the preparation of crystalline silicate ZSM-48 by the preferred method described above.

The linear diquaternary ammonium compounds employed in these zeolite crystallization examples had the structure

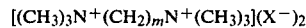

$[(CH_3)_3N^+(CH_2)_mN^+(CH_3)_3](X^-)_2$ with $m = 5, 6, 8, 9$ or $10$ and $X = Br$ and $I$. "Diquat-6" ($m=6$) was used as the iodide salt whereas the other organic directing agents ($m=5, 8, 9$ or $10$) were used as the bromide salts.

The other mixture components in Examples 1, 2, 3 and 6 were silica sol (30% $SiO_2$), NaOH and water. No separate aluminum source was added to these mixtuers. For Example 9, the other mixture components were silica sol (30% $SiO_2$), $NaAlO_2$, NaOH and water.

In the case of Examples 4 and 5, Q-Brand sodium silicate (27.8% $SiO_2$; 8.4% $Na_2O$; 63.8% $H_2O$) and water were other mixture components. No separate aluminum source was added to these mixtures, but $H_2SO_4$ was added to adjust the $OH^-/SiO_2$ mole ratios to the desired levels.

For Examples 7, 8 and 10 through 15, the other mixture components were Q-Brand sodium silicate, $Al_2(SO_4)_3 \cdot 16H_2O$, and water. Again the desired $OH^-/SiO_2$ mole ratios in the initial hydrogels were attained by addition of $H_2SO_4$.

In each example listed in Table 2, the crystallization time is given together with the resulting zeolite product. The crystallization temperature was maintained at 160° C., with stirring, during crystallization for each experiment. Note in Example 15 that when the $SiO_2/Al_2O_3$ ratio of the reaction mixture is less than 100, synthesis with a diquaternary cation, at the proper composition, produces a different cyrstalline silicate framework, not ZSM-48.

The final product of each experiment was filtered, washed with water, and dried at 110° C.

TABLE 2

| | | Reaction Mixture Composition (Mole Ratios) | | | | | Reaction | |
|---|---|---|---|---|---|---|---|---|
| Example | R | $SiO_2/Al_2O_3$ | $H_2O/SiO_2$ | $OH^-/SiO_2$ | $Na^+/SiO_2$ | $R/SiO_2$ | Time, days | Product |
| 1 | Diquat-6 | infinite | 40 | 0.20 | 0.20 | 0.10 | 3 | ZSM-48 |
| 2 | Diquat-6 | infinite | 40 | 0.30 | 0.30 | 0.10 | 4 | ZSM-48 |
| 3 | Diquat-5 | infinite | 40 | 0.30 | 0.30 | 0.10 | 4 | ZSM-48 |
| 4 | Diquat-8 | infinite | 40 | 0.30 | 0.59 | 0.10 | 5 | ZSM-48 |
| 5 | Diquat-10 | infinite | 40 | 0.20 | 0.59 | 0.10 | 7 | ZSM-48 |
| 6 | Diquat-9 | infinite | 40 | 0.20 | 0.20 | 0.10 | 5 | ZSM-48 |
| 7 | Diquat-6 | 500 | 40 | 0.30 | 0.59 | 0.10 | 3 | ZSM-48 |
| 8 | Diquat-6 | 300 | 40 | 0.30 | 0.59 | 0.10 | 3 | ZSM-48 |
| 9 | Diquat-8 | 200 | 40 | 0.20 | 0.24 | 0.10 | 3 | ZSM-48 |
| 10 | Diquat-6 | 200 | 40 | 0.20 | 0.59 | 0.10 | 6 | ZSM-48 |
| 11 | Diquat-6 | 200 | 40 | 0.20 | 0.59 | 0.10 | 6 | ZSM-48 |
| 12 | Diquat-6 | 180 | 40 | 0.30 | 0.59 | 0.10 | 3 | ZSM-48 |
| 13 | Diquat-6 | 150 | 40 | 0.20 | 0.59 | 0.10 | 4 | ZSM-48 |
| 14 | Diquat-6 | 100 | 40 | 0.20 | 0.59 | 0.10 | 3 | ZSM-48 |
| 15 | Diquat-6 | 90 | 40 | 0.30 | 0.59 | 0.10 | 4 | Other Crystalline Silicate |

As-synthesized crystalline products from certain of the foregoing examples were submitted for chemical analysis and X-ray diffraction analysis. Table 3 lists the analytical compositions of these products. The "composition" information in Table 3 was calculated on the basis of 100 (SiO$_2$+AlO$_4$) tetrahedra.

TABLE 3

| | | | | Composition | | | |
|---|---|---|---|---|---|---|---|
| | Moles per mole Al$_2$O$_3$ | | | | | | Molecules |
| Example | C/N | N$_2$O: | Na$_2$O: | SiO$_2$ | Al/100 T$_d$ | Na+/100 T$_d$ | N/100 T$_d$ | R/100 T$_d$ |
| 1 | 5.6 | 5.6 | 3.5 | 207 | 0.96 | 3.3 | 5.3 | 2.5 |
| 2 | 5.1 | 12.2 | 2.2 | 362 | 0.55 | 2.4 | 6.7 | 2.8 |
| 4 | 7.8 | 15.5 | 2.0 | 694 | 0.29 | 5.7 | 4.4 | 2.5 |
| 5 | 8.7 | 18.0 | 5.7 | 979 | 0.20 | 1.2 | 3.7 | 2.0 |
| 7 | 5.9 | 4.5 | 2.2 | 184 | 1.1 | 2.4 | 4.8 | 2.4 |
| 8 | 6.3 | 2.6 | 0.4 | 119 | 1.6 | 0.7 | 4.3 | 2.3 |
| 10 | 5.8 | 3.1 | 0.11 | 121 | 1.6 | 1.6 | 5.0 | 2.4 |
| 11 | 5.5 | 3.7 | 0.53 | 142 | 1.4 | 0.7 | 3.2 | 1.5 |
| 12 | n.a. | n.a. | n.a. | 98 | 2.0 | n.a. | n.a. | n.a. |
| 13 | n.a. | 3.5 | 0.34 | 113 | 1.7 | 0.6 | 6.1 | n.a. |
| 14 | 6.6 | 2.3 | 0.87 | 85 | 2.3 | 2.0 | 5.2 | 2.9 |

The process of this invention is conducted such that conversion of the lower olefin feedstock, e.g., one containing one or more C$_{2-8}$ olefins, is carried out in the vapor-phase by contact in a reaction zone, such as, for example, a fixed bed containing ZSM-48 crystal, under conversion effective conditions. This process can be conducted in either batch or fluid bed operation with attendant benefits of either operation readily obtainable. The lower olefin, e.g., can be made up of ethylene, propylene, n- and isobutene-1, cis and trans n-butene-2, n- and isopentenes, n- and isoheptenes, mixtures of these and other olefins such as off-gas containing ethylene and propylene, naphtha cracker off-gas containing lower olefins or light catalytic cracked gasoline containing pentenes, hexenes and heptenes.

The present process is advantageously carried out at a temperature between about 350° F and 1000° F, preferably from about 400° F to about 500° F, and at pressures ranging from about 200 up to about 2000 psig, preferably from about 700 to about 1000 psig. The weight hourly space velocity (WHSV) is advantageously maintained at from about 0.1 to about 10, preferably from about 0.3 to about 4. Within these limits the conditions of temperature and pressure will vary considerably depending upon equilibrium considerations, exact feed material, and presence or absence of diluents, such as, for example, C$_1$–C$_4$ paraffins, such as methane, ethane, propane, isobutane and n-butane; and hydrogen sulfide. The amount of diluent which can be present in the improved process of this invention is not narrowly critical and may vary within the range of 0 to about 90 weight percent based on the weight of olefin feedstock. Preferably, the amount of diluent is within the range of from about 20 to about 60 weight percent.

Optimum conditions are those in which maximum yields of gasoline, distillate and lube products are obtained and hence considerations of temperature and pressure will vary within a range of conversion levels designed to provide the highest selectivity and maximum yield.

The process can also be carried out with separation of the product into at least two fractions, e.g., a high boiling, lubricant range fraction made up primarily of C$_{19}$+hydrocarbons and a lower boiling fraction made up primarily of C$_{19}$+hydrocarbons and a lower boiling fraction made up primarily of C$_{6-18}$ hydrocarbons which is recycled. Such a process utilizing HZSM-5 catalyst is described in U.S. Pat. No. 4,547,612, the contents of which are incorporated by reference herein.

The following example is illustrative of the method herewith for converting light olefins to gasoline, distillate and lube range hydrocarbons employing crystalline silicate ZSM-48.

EXAMPLE 16

The use of zeolite ZSM-48 is compared with the results of olefin conversion employing ZSM-5 under substantially the same process conditions.

Propylene was converted at 230° C., 400 psig and WHSV of 0.3 in the presence of the ZSM-48 catalyst of Example 11 to provide gasoline and distillate range hydrocarbons and a 650° F+ lube fraction.

In Table 4 below, the product distribution and product properties using ZSM-48 are compared with those achieved by conversion over ZSM-5.

TABLE 4

Olefin Conversion To Gasoline, Distillate and Lube Fractions: Product Distribution and Lube Properties

| | ZSM-48 | ZSM-5 |
|---|---|---|
| Catalyst | | |
| SiO$_2$/Al$_2$O$_3$ | 142 | 142 |
| Products: | | |
| C1–C6 | 8.8 | 3.7 |
| C6–330° F. | 19.8 | 21.8 |
| 330–650° F. | 46.6 | 47.6 |
| 650° F.+ | 24.8 | 26.8 |
| VI | 74.1 | 74.1 |
| Properties, 650° F.+ bottoms: | | |
| KV at 40° C. | 33.49 | 22.45 |
| KV at 100° C. | 5.17 | 4.15 |
| Viscosity Index | 74.1 | 74.1 |
| SUS at 100° F. | 173.6 | 117.6 |

What is claimed is:

1. A process for converting light olefin to gasoline, distillate and lube range hydrocarbons which comprises contacting an olefin feedstock containing predominantly lower olefin with acidic zeolite ZSM-48, wherein the composition of the as-synthesized ZSM-48 in terms of moles of anhydrous oxides per 100 moles of silica is (0.05 to 5) R$_2$:(0.1 to 10) M$_{2/n}$O:(0.2 to 1)
 Me$_2$O$_3$:(100)SiO$_2$ wherein R is a cation derived from an organic directing agent selected from the group consisting of a mixture of a C$_{2-12}$ alkyl-amine and a tetramethylammonium compound and a linear diquaternary ammonium compound, M is a cation of valence n and Me$_2$O$_3$ is the oxide of at least one metal selected from aluminum, gallium and iron, at elevated pressure and temperature to provide a product containing gasoline and distillate range hydrocarbons at a 650° F+ lube fraction.

2. The process of claim 1 wherein the olefin is one or a mixture of $C_{2-4}$ olefins.

3. The process of claim 1 wherein the feedstock contains propylene.

4. The process of claim 1 wherein the gasoline and/or distillate range hdyrocarbons are separated from the 650° F+ lube fraction and recycled.

5. The process of claim 1 wherein the organic directing agent is a linear diquaternary ammonium compound is expressed by the formula:

$$[(R')_3N^+(Z)_mN^+(R')_3](X^-)_2$$

wherein R' is aklyl of from 1 to 20 carbon atoms, heteroalkyl of from 1 to 20 carbon atoms, aryl, heteroaryl, cycloalkyl of from 3 to 6 carbon atoms, cycloheteroalkyl of from 3 to 6 carbon atoms, or combinations thereof; N is the quadricoordinte element nitrogen, or the heteroatom nitrogen in an alicyclic, heteroalicyclic or heteroaromatic structure X is an anion; Z is a bridging member selected from the group consisting of alkyl of from 1 to 20 carbon atoms, alkenyl of from 2 to 20 carbon atoms, aryl, heteroalkyl of from 1 to 20 carbon atoms, heteroalkenyl of from 2 to 20 carbon atoms and heteroaryl; and m is 5, 6, 8, 9 or 10.

6. The process of claim 5 wherein X is halide and R' and Z are alkyl of 1 to 4 carbon atoms.

7. The process of claim 6 wherein X is iodide or bromide, and R' and Z are methyl.

8. The process of claim 1 carried out at about a temperature of from 350° F to about 600° F.

9. The process of claim 1 carried out at a temperature of from about 400° F to about 500° F.

10. The process of claim 1 carried out at a pressure of from about 200 psig to about 2000 psig.

11. The process of claim 1 carried out at a pressure of from about 200 psig to about 1000 psig.

12. The process of claim 1 carried out at a weight hourly space velocity of from about 0.1 to about 10.

13. The process of claim 1 carried out at a weight hourly space velocity of from about 0.2 to about 4.

14. The process of claim 1 carried out at a temperature of from about 350° F to about 600° F, a pressure of at least 200 psig, and a weight hourly space velocity of from about 0.1 to about 10.

15. The process of claim 1 carried out at a temperature of from about 400° F to about 500° F, a pressure of from about 700 psig to about 1000 psig and a weight hourly space velocity of from about 0.2 to about 4.

16. A process for converting light olefin to gasoline, distillate and lube range hydrocarbons which comprises contacting an olefin feedstock containing predominantly lower olefin with a catalyst consisting essentially of an acidic crystalline metallo-silicate zeolite exhibiting a characteristic X-ray diffraction pattern as shown in Table I of the specification at elevated pressure and temperature to provide a product containing gasoline and distillate range hydrocarbons and a 650° F+ lube fraction, said zeolite containing at least one trivalent metal oxide selected from oxides of aluminum, gallium, iron and boron and having a molar ratio of silica to said trivalent metal oxide less than 500.

17. The process of claim 16 wherein the 650° F+ lube fraction has a SUS viscosity of at least 173.6 at 100° F.

18. The process of claim 16 wherein the zeolite consists essentially of alumino-silicate ZSM-48 having a silica-to-alumina molar ratio from about 100 to less than 500.

19. A process for producing high viscosity lubricant range hydrocarbons from lower olefin feedstock by contacting the feedstock under conversion conditions at elevated temperature up to about 600° F and pressure greater than 200 psig with an acidic crystalline alumino-silicate zeolite having the structure of ZSM-48 and having a silica-to-alumina molar ratio less than 500.

* * * * *

UNITED STATES PATENT AND TRADEMARK OFFICE
CERTIFICATE OF CORRECTION

PATENT NO. : 4,665,250

DATED : May 12, 1987

INVENTOR(S) : Cynthia T-W Chu and Ernest W. Valyocsik

It is certified that error appears in the above-identified patent and that said Letters Patent is hereby corrected as shown below:

Column 2, line 67, after "oxide," insert --boria,--.

Column 9, line 6, "hdyrocarbons" should be --hydrocarbons--.

Signed and Sealed this

Fifteenth Day of December, 1987

*Attest:*

DONALD J. QUIGG

*Attesting Officer*  *Commissioner of Patents and Trademarks*